(12) United States Patent
Rapaport

(10) Patent No.: US 8,303,934 B2
(45) Date of Patent: Nov. 6, 2012

(54) METHODS AND COMPOSITIONS OF [32P]-LABELED ADENINE NUCLEOTIDES FOR THE TREATMENT OF ATHEROSCLEROSIS, VASCULAR ARTERIAL DISEASES AND CORONARY ARTERY DISEASES

(76) Inventor: Eliezer Rapaport, Belmont, MA (US)

( * ) Notice: Subject to any disclaimer, the term of this patent is extended or adjusted under 35 U.S.C. 154(b) by 0 days.

(21) Appl. No.: 13/185,083

(22) Filed: Jul. 18, 2011

(65) Prior Publication Data

US 2012/0128582 A1 May 24, 2012

(51) Int. Cl.
*A61K 51/00* (2006.01)
(52) U.S. Cl. ...................................... 424/1.65; 424/1.73
(58) Field of Classification Search ........................ None
See application file for complete search history.

(56) References Cited

U.S. PATENT DOCUMENTS

| 6,299,857 B1 * | 10/2001 | Elmaleh et al. ............... 424/1.73 |
| 2004/0067197 A1 * | 4/2004 | Leclerc et al. ................ 424/1.73 |
| 2005/0079225 A1 * | 4/2005 | Rapaport ....................... 424/601 |

OTHER PUBLICATIONS

"Arterial thrombotic syndromes in cancer patients," Brenner, B., Hoemostasis 31(suppl. 1): 43-44 (2001).*
"Atherosclerosis and Vascular Aging as Modifiers of Tumor Progression, Angiogenesis, and Responsiveness to Therapy," Klement, H., et al., Amer. J. Path. 171(4): 1342-1351 (2007).*
"Oligoradionuclidetherapy using radiolabeled antisense oligodeoxynucleotide phosphorothioates," Kairemo, K., et al., Anti-Cancer Drug Design 11: 439-449 (1996).*
Cheng Y et al. "Strong Inhibition of Xenografted Tumor Growth by Low-Level Doses of [32P]ATP," Oncotarget. Jun. 2011;2(6):461-466.
Elmaleh DR et al. "99mTc-labeled nucleotides as tumor-seeking radiodiagnostic agents," Proc Natl Acad Sci USA. 1984; 81(3):918-921.
Elmaleh DR et al. "Rapid noninvasive detection of experimental atherosclerotic lesions with novel 99mTc-labeled diadenosine tetraphosphates," Proc Natl Acad Sci USA. 1998; 95(2):691-695.
Elmaleh DR et al. "Detection of inflamed atherosclerotic regions with diadenosine-5',5'''-P1,P4-tetraphosphate (Ap4A) and positron emission tomography, Proc Nat Acad Sci USA 2006; 103(43):15992-15996.
Feng L et al. "Vascular CD39/ENTPD1 directly promotes tumor cell growth by scavenging extracellular adenosine triphosphate," Neoplasia. Mar. 2011;13(3):206-216.
Guns PJ et al. "P2Y receptors and atherosclerosis in apolipoprotein E-deficient mice," Br J Pharmacol. Jan. 1, 2010;159(2):326-336.
Jacobson KA et al. "P2Y nucleotide receptors: Promise of therapeutic application," Drug Discovery Today. Jul. 2010 ; 15(13-14): 570-578.
Khakh BS et al. "The double life of ATP," Sci. Am. 2009; Dec;301(6):84-90 and 92.
Kukulska A et al. "Radioiodine thyroid remnant ablation in patients with differentiated thyroid carcinoma (DTC): prospective comparison of long-term outcomes of treatment with 30, 60 and 100 mCi," Thyroid Res. Nov. 1, 2010;3(1):9, 1-4.
Rapaport E et al. "HeLa cell DNA polymerase alpha is tightly associated with tryptophanyl-tRNA synthetase and diadenosine 5',5'''-P1,P4-tetraphosphate binding activities, Proc Nat Acad Sci USA 1981; 78(2):838-842.

* cited by examiner

*Primary Examiner* — David J Blanchard
*Assistant Examiner* — Daniel F Coughlin
(74) *Attorney, Agent, or Firm* — Connolly Bove Lodge & Hutz LLP

(57) ABSTRACT

A method for the treatment of atherosclerosis. The method includes the administration of a 32P-labeled agent as a beta emitter, such as 32P-labeled ATP or other 32P-labeled adenine nucleotides, whereby the 32P-labeled agent seeks and then permeates the atherosclerotic plaque en bloc without prior degradation. The accumulation of the 32P-labeled agent in the atherosclerotic plaque is achieved at time points whereby the 32P-labeled agent is cleared from the blood. Thus, radionuclide-labeled adenine nucleotides accumulate with high specificity in atherosclerotic lesions and in the heart. The beta particles (electrons) emitted by the 32P-label have a maximal path distance of about 0.5 cm and their energy preferentially destroy cells present in the atherosclerotic plaque without affecting vessel integrity or inducing arterial thrombosis.

12 Claims, No Drawings

METHODS AND COMPOSITIONS OF [32P]-LABELED ADENINE NUCLEOTIDES FOR THE TREATMENT OF ATHEROSCLEROSIS, VASCULAR ARTERIAL DISEASES AND CORONARY ARTERY DISEASES

BACKGROUND

Atherosclerosis is usually found in most major arteries, initially it is asymptomatic and not detected by most diagnostic methods. Atheroma in arm, or more often in leg arteries, which produces decreased blood flow is called peripheral arterial occlusive disease (PAOD). Cardiovascular disease including atherosclerosis is a leading cause of death in the developed world. According to United States data for the year 2004, for about 65% of men and 47% of women, the first symptom of atherosclerotic cardiovascular disease is a heart attack or sudden cardiac death (death within one hour of onset of the symptoms). Patients having such disease usually have narrowing or closing (stenosis) in one or more arteries.

The atherogenic process involves sequestration of partially oxidized lipids in the vessel wall, leading to endothelial injury that promotes adherence of mononuclear cells and platelets and contributes to phenotypic transformation of medial smooth muscle cells (SMCs) from adult to embryonic forms. The transformed smooth muscle cells proliferate and migrate to the intima of the vessel in parallel with accumulation of lipids by monocytes, causing the formation of foam cells. Other processes of plaque formation, involve T lymphocytes, platelets, cytokine release, and growth factors, which enhance migration and proliferation of SMCs. The proliferation and migration of SMCs are central to the pathogenesis of coronary artery disease. The present disclosure relates generally to methods of arresting and killing SMCs by exposing the cells to very low concentrations of an anti-proliferative, cytotoxic agent. Methods detailing the use of low levels of cytotoxic agents such as Paclitaxel (Taxol) or medical devices that are capable of providing sustained release of one or more cytotoxic therapeutic agents over a time period and in an amount effective to inhibit SMCs proliferation and/or migration are known (e.g. U.S. Pat. No. 7,919,108).

A recent review of purinergic (ATP) drugs in development focuses on synthetic agonists and antagonists of specific P2Y receptors that play a role in atherosclerosis, vascular injury, plaque formation and thrombosis (Jacobson K A, Boeynaems J-M: P2Y nucleotide receptors: Promise of therapeutic application. Drug Discov Today. 2010 July; 15(13-14): 570-578). P2Y12 receptors control platelet aggregation and antagonists of P2Y12 receptor similar to Clopidogrel (Plavix) are tested by a variety of pharmaceutical companies as anti-thrombotic drugs. P2Y receptors are involved at various steps in the inflammatory process. ATP released from neutrophils amplifies their attraction by providing chemotactic signals and its release from apoptotic cells constitutes a "find-me signal" for monocytes/macrophages. These actions are abrogated in leukocytes from P2Y2 -/- mice. Nucleotides upregulate the expression on endothelial cells of VCAM-1, that plays a crucial role in the tissue infiltration of eosinophils and monocytes. This action is P2Y2 receptor-mediated in coronary arteries, however P2Y4 and P2Y6 receptors might also be involved in other vascular beds. The approach disclosed in the present application is different in at least two aspects from the common purine drug discovery process. Applicant is not developing a new chemical entity but rather utilizing the natural agonist, ATP, for seeking and permeating into the atherosclerotic plaque. The mechanism in large part involves interactions with purine receptors. Once inside the plaque, the beta emission from the 32P-radioactive label causes destruction of cells that participate in the build-up of the plaque.

The utilization of non-32P-labeled adenine nucleotides in tumor imaging (Elmaleh D R, Zamecnik P C, Castronovo F P, Jr, Strauss H W, Rapaport E: 99mTc-labeled nucleotides as tumor-seeking radiodiagnostic agents. Proc Natl Acad Sci USA. 1984; 81(3): 918-92 and U.S. Pat. No. 6,299,857) is a method partly established by applicant. Subsequently, the administration of non-32P-labeled, radionuclide-labeled adenine nucleotides, which are derivatives of ATP, demonstrated the utility of these agents in the noninvasive imaging of atherosclerotic lesions (Elmaleh D R, Narula J, Babich J W, Petrov A, Fischman A J, Khaw B A, Rapaport E, Zamecnik P C: Rapid noninvasive detection of experimental atherosclerotic lesions with novel 99mTc-labeled diadenosine tetraphosphates. Proc Natl Acad Sci USA. 1998; 95(2): 691-695 and Elmaleh D R, Fischman A J, Tawakol A, Zhu A, Shoup T M, Hoffman U, Brownell A-L, Zamecnik P C: Detection of inflamed atherosclerotic regions with diadenosine-5',5'''-P1, P4-tetraphosphate (Ap4A) and positron emission tomography. Proc Nat Acad Sci USA 2006; 103(43): 15992-15996). Thus, radionuclide-labeled adenine nucleotides, accumulates with high specificity in atherosclerotic lesions and in the heart.

Adenine nucleotides and ATP in particular, in a variety of physical and chemical forms including radio-nuclides were claimed and described as anti-tumor agents suitable for arrest of tumor cells without substantially affecting normal tissue (Rapaport E., U.S. Pat. Nos. 4,880,918; 5,049,372; 7,671,038; 7,879,814). Examples of such materials are adenosine 5'-monophosphate (AMP), adenosine 5'-diphosphate (ADP) and adenosine 5'-triphosphate (ATP). In addition, pharmaceutically acceptable salts, or metal complexes, or chelates, or liposomes, or radionuclides of the above compounds were recited either in the claims or in the specification of the above mentioned patents (please note U.S. Pat. No. 7,879,814). A radionuclide labeled ATP, [32P]ATP, was shown recently to be very active as an anti-tumor cytotoxic agent in established human xenographed tumors in athymic mice (Cheng Y, Yang J, Agarwal R, Green G M, Mease R C, Pomper M G, Meltzer S J, Abraham J M.: Strong Inhibition of Xenografted Tumor Growth by Low-Level Doses of [32P]ATP. Oncotarget. 2011 June; 2(6): 461-466).

Preparations containing the above ingredients can be employed in a variety of conventional pharmaceutical preparations. These preparations can contain organic or inorganic material suitable for internal administration. The high solubility of AMP and/or ADP and/or ATP salts in isotonic aqueous solutions of sodium chloride enables administration of these agents in the form of injection or infusion of single or multiple doses. The injection or infusion can be intraperitoneal, intravenous, or intra-arterial.

The established treatment of atherosclerosis and coronary artery disease consists of treatments of a variety of its underlying causes. Once this approach fails, the more direct methods undertaken are angioplasty (PTA or percutaneous transluminal angioplasty), which can be done on solitary lesions in large arteries, such as the femoral artery. Angioplasty may not have sustained benefits. Another approach involves plaque excision, whereby the plaque is scraped off out of the inside of the vessel wall. Occasionally, bypass grafting is needed to circumvent a seriously stenosed area of the arterial vasculature. Generally, the saphenous vein is used, although artificial (Gore-Tex) material is often used for large tracts when the veins are of lesser quality. Rarely, sympathectomy is used—removing the nerves that make arteries contract, effectively leading to vasodilatation. Arterial thrombosis or embolism has a dismal prognosis, but is occasionally treated successfully with thrombolytic agents.

Many treatments of the vascular or other systems entail the introduction of a device such as a stent, a catheter, a balloon, a wire guide, a cannula or the like. These devices are used to introduce cytotoxic drugs into injured arteries at a specific location. U.S. Pat. No. 7,919,108 discloses delivery of a therapeutic agent from an implantable medical device that can be desirable for a variety of applications. Occasionally, angioplasty may be followed by an abrupt closure of the vessel or by a more gradual closure of the vessel, commonly known as restenosis. Acute closure may result from an elastic rebound of the vessel wall and/or by the deposition of blood platelets and fibrin along a damaged length of the newly opened blood vessel. In addition, restenosis may result from the natural healing reaction to the injury to the vessel wall (known as intimal hyperplasia), which can involve the migration and proliferation of medial smooth muscle cells that continues until the vessel is again occluded. To prevent such vessel occlusion, stents have been implanted within a body vessel. However, restenosis may still occur over the length of the stent and/or past the ends of the stent where the inward forces of the stenosis are unopposed. To reduce this problem, one or more therapeutic agents may be administered to the patient. For example, a therapeutic agent may be administered systemically or locally administered through a catheter positioned within the body vessel near the stent, or coated on the stent itself

[99mTc]Ap4A and similar agents were successfully utilized as radiopharmaceuticals, which were shown to have potential both as radiodiagnostic agents for the rapid detection of atherosclerotic plaques and for probing the fundamental pathophysiology of atherogenesis (Elmaleh, 1998; supra). The accumulation of [18F]AppCHFppA in macrophage-rich atherosclerotic plaques was quantified noninvasively with PET (Elmaleh 2006; supra). Hence, [18F]AppCHFppA holds promise for the noninvasive characterization of vascular inflammation.

SUMMARY OF THE DISCLOSURE

Disclosed herein is a method for treating cardiovascular disease and/or atherosclerosis and/or vascular inflammation and/or stenosis by administering to a human patient in need thereof a member selected from the group consisting of a radio-nuclide-labeled adenosine 5'-monophosphate; adenosine 5'-diphosphate; adenosine 5'-triphosphate; diadenosine 5',5"-P1,P4-tetraphosphate; and pharmaceutically accepted salts thereof or; metal complexes thereof or; chelates thereof or; and liposomes thereof, or a mixture of two or more thereof.

Adenosine 5'-triphosphate (ATP) is an established antitumor agent showing specificity towards tumor cells without adversely affecting most normal cells. Other phosphorylated adenosine derivatives, adenine nucleotides, act by similar mechanisms to arrest the growth of tumor cells. Radio-nuclides of ATP or other adenine nucleotides were claimed as cytotoxic agents in several previously issued patents to applicant. In addition, the specifications of several issued U.S. patents to applicant disclose the effects of ATP in the form of radio-nuclides. However, ATP is also a known stimulator of SMCs proliferation and migration. There is evidence for an important role for ATP and other adenine nucleotides in supporting the development of atherosclerotic plaques. Anti-inflammatory and anti-sclerotic plaque drug research focuses on antagonists of ATP rather than on ATP or its agonists.

Recent results suggest involvement of ATP receptors, particularly P2Y2, P2Y4 and P2Y6 receptors in the formation of atherosclerosis, and warrant further focus on selective purine receptor antagonists (Guns P J, Hendrickx J, Van Assche T, Fransen P, Bult H: P2Y receptors and atherosclerosis in apolipoprotein E-deficient mice. Br J Pharmacol. 2010 Jan. 1; 159(2): 326-36). These P2Y receptors, which are present on SMCs and which seemingly make antagonists of ATP, rather than ATP itself, useful agents active in the treatment of atherosclerosis (see Jacobson and Boeynaems; 2010, Supra). The effects of extracellular ATP in receptor-mediated promotion of vascular inflammation and restenosis are well established (Khakh B S, Burnstock G.: The double life of ATP. Sci Am. 2009 December; 301(6): 84-90, 92).

Thus, all the prior art teaches away from using ATP or its derivatives or its radio-nuclides in the treatment of atherosclerosis and coronary artery disease. The present disclosure is based on the applicant's many years of experience in the effects of ATP and other adenine nucleotides on normal and cancerous tissues in vivo and the ability of ATP to preferentially permeate atherosclerotic plaques in in vivo models of atherosclerosis.

[32P]-labeled ATP possesses two advantages over other agents known in the art. It is an effective cytotoxic agent and unlike other cytotoxic agents (e.g. Taxane coated stents) it directs itself and accumulates in the target—the atherosclerotic plaque. Therefore, the present disclosure teaches the novel utilization of beta emitters [32P]ATP and its [32P]-labeled derivatives for the treatment of atherosclerosis, cardiovascular disease, vascular inflammation, atherosclerotic plaques and thrombosis.

The present application, however, utilizes a class of beta emitting cytotoxic agents that after being administered at a remote site are capable of accumulating in an atherosclerotic plaque. The short distance beta radiation then acts in destroying cells causing cardiovascular lesions and inflammation. As importantly, the beta energy of electrons emitted by [32P] produces a "bystander effect" whereby the cytotoxic agent destroys cells neighboring to the area where it penetrated.

DESCRIPTION OF THE BEST AND VARIOUS EMBODIMENTS

The foregoing and other objects, aspects and advantages will be better understood from the following detailed description of the best and various embodiments. Throughout the various views and illustrative embodiments of the present disclosure, like reference numbers are used to designate like elements.

For convenience, the meaning of certain terms and phrases employed in the following specification and appended claims are provided below:

"Cardiovascular disease"or "cardiovascular lesion"refers to any of a variety of disease or lesions to the heart or vasculature of a subject. Examples include atherosclerosis (i.e. thickening and hardening of arteries due to plaque formation) and related disorders resulting from occluded blood flow (e.g. angina, cerebral ischemia, renal hypertension, ischemic heart disease, stroke) and thrombus formation (e.g. Deep Vein Thrombosis (DVT)). "Stenosis" refers to an abnormal narrowing of a blood vessel. "vascular inflammation" refers to vascular tissue damage in a subject, which may result from a number of causes (e.g. microbial infection, autoimmune processes, any injury or trauma, etc). Regardless of cause, the vascular inflammatory response consists of a complicated set of functional and cellular adjustments involving changes in microcirculation, movement of fluids, proliferation of smooth muscle cells, generation of foam cells and influx and activation of inflammatory cells. "thrombus" refers to a clot of blood formed within a blood vessel from a plaque and which remains attached to its place of origin.

The Treatment of Atherosclerotic Plaques. [gamma-32P] ATP 3000 Ci/mmol, 5 mCi/ml of Tricine buffer (10-50 mM, pH 7.6), [gamma-32P]ATP 6000 Ci/mmol, 10 mCi/ml of Tricine buffer (10-50 mM, pH 7.6) and [alpha-32P]ATP 3000 Ci/mmol, 5 mCi/ml of Tricine buffer (10-50 mM, pH 7.6) are purchased from Perkin Elmer (New England Nuclear). Radioactively labeled nucleotides at similar specific radioactivities are available from other suppliers. [alpha -32P]AMP and [beta-32P]ADP are available from commercial sources. [32P]Ap4A (diadenosine 5',5"- P1,P4-tetraphosphate) of similar specific radioactivities to those of [32P]ATP is synthesized from [32P]ATP and unlabeled AMP according to Rapaport et al., (E Rapaport, P C Zamecnik, and E F Baril:

HeLa cell DNA polymerase alpha is tightly associated with tryptophanyl-tRNA synthetase and diadenosine 5',5"-P1,P4-tetraphosphate binding activities. Proc. Natl. Acad. Sci. USA 1981; 78 (2) 838-842).

For cardiovascular disease, high specific radioactivities, active agents cited in the disclosure, may be used in accordance with the methods of the disclosure by those skilled in the art. The results of the treatment are assessed by PET, or other routine imaging techniques, which are identical to procedures used for assessing baseline, before treatment. These include a gamma camera, a PET apparatus, a SPECT apparatus, and the like. The average beta energy of electrons emitted by [32P]ATP, or 32P- labeled adenine nucleotides is above the beta energy emitted by 131-labeled Iodine. Thus, the penetration of the electrons is longer, enabling better focus on the disease target. Since the half-life of 32-P is longer than that of 131-I, 32-P has another advantage over 131-I. An example of treatment of cancerous thyroid remnant in human patients with 30, 60 and 100 mCi of 131-I is enclosed (Kukulska A, Krajewska J, Gawkowska-Suwińska M, Pilch Z, Paliczka-Cieslik E, Roskosz J, Handkiewicz-Junak D, Jarzab M, Gubala F, Jarzab B.: Radioiodine thyroid remnant ablation in patients with differentiated thyroid carcinoma (DTC): prospective comparison of long-term outcomes of treatment with 30, 60 and 100 mCi. Thyroid. Res. 2010 November 1; 3(1): 9).

The administration of [32P]ATP or other [32P]-adenine nucleotides such as, but not limited to [32P]Ap4A or [32P] AMP or [32P]ADP, is a clear case whereby the therapeutic agent is not delivered to the site of vascular injury by any of the devices listed above. Rather [32P]ATP and other [32P]-labeled adenine nucleotides act in seeking and homing onto an atherosclerotic plaque or stenosed area of arterial vasculature when administered at a remote site. This property along with the cytotoxic action of [32P]ATP and related adenine nucleotides, makes these agents attractive intravascular therapeutic agents.

For a typical treatment procedure active agent or control are infused or injected into patient suffering from atherosclerotic lesions. Typical administration of [32P]ATP is performed by administering 0.1-100 milliCuries of active agent in 1-500 ml of saline or phosphate buffered saline or Balanced Salt Solution. Preferred administration is performed by continuous intravenous infusion. Serial imaging starting one week after the administration of therapeutic agent are taken and compared to images taken before administration of therapeutic agent.

It is expected pursuant to the present disclosure that a human patient suffering from cardiovascular disease and/or vascular inflammation can be treated by plaque-seeking agents whereby being administered a member selected from the group consisting of: a [32P]adenine nucleotide wherein said 32P-labeled adenine nucleotide containing adenosine moiety(ies) and [32P]phosphate moiety(ies). After administration of active agent, the portion of agent that is not retained in the atherosclerotic plaque, is rapidly degraded to adenosine and [32P]-labeled inorganic phosphate, which are rapidly removed. The intravascular catabolic activities, mostly CD39 (NTPDase) and CD73 (5'-Nucleotidase), which catalyze the degradation of active agents, are strong inside the vascular bed (Feng L, Sun X, Csizmadia E, Han L, Bian S, Murakami T, Wang X, Robson S C, Wu Y.: Vascular CD39/ENTPD1 directly promotes tumor cell growth by scavenging extracellular adenosine triphosphate. Neoplasia. 2011 March; 13(3): 206-16).

Examples of active agents are, but not limited to, [32P] adenosine 5'-monophosphate (AMP), [32P]adenosine 5'-diphosphate (ADP), [32P]adenosine 5'-triphosphate (ATP) and [32P]diadenosine-tetraphosphate (Ap4A). In addition, pharmaceutically acceptable salts, or metal complexes, or chelates, or liposomes, of the above compounds can be used. [32P]-labeled active agent can be administered under a variety of schedules and number of cycles with the results being assessed by routine imaging techniques.

Preparations containing the above ingredients can be employed in a variety of conventional pharmaceutical preparations. These preparations can contain organic or inorganic material suitable for internal administration. The high solubility of AMP and/or ADP and/or ATP salts labeled with 32P in isotonic aqueous solutions of sodium chloride enable administration of these agents in the form of injection or infusion of single or multiple doses. The injection or infusion can be intramuscular, intraperitoneal, intravenous, or intra-arterial. Since beta emission travels a short distance of a few millimeters, the active agents can be used in a patch for continuous administration. Any one of the 32P-therapeutic agents can be administered to a subject in accordance with any means that facilitates accumulation of the agent in a subject's cardiovascular system. Preferably, the radiophatmaceutical agent, which assesses the disclosure is administered by arterial or venous injection, and has been formulated as a sterile, pyrogen-free, parenterally acceptable aqueous solution. The preparation of such parenterally acceptable solutions, having due regard to pH, isotonicity, stability, and the like, is within the skill in the art. A preferred formulation for intravenous injection should contain, in addition to the therapeutic agent and the cardiovascular imaging agent, an isotonic vehicle such as Sodium Chloride Injection, Ringer's Injection, Dextrose Injection, Dextrose and Sodium Chloride Injection, Lactated Ringer's Injection, or other vehicle as known in the art.

The embodiments described hereinabove are further intended to explain best modes known of practicing it and to enable others skilled in the art to utilize the disclosure in such, or other, embodiments and with the various modifications required by the particular applications or uses. Accordingly, the description is not intended to limit it to the form disclosed herein. Also, it is intended that the appended claims be construed to include alternative embodiments.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purpose, as if each individual publication, patent or patent application were specifically and individually indicated to be incorporated by reference. In the case of inconsistencies, the present disclosure will prevail.

REFERENCES

1. Jacobson K A, Boeynaems J-M: P2Y nucleotide receptors: Promise of therapeutic application. Drug Discov Today. 2010 July; 15(13-14): 570-578.
2. Elmaleh DR, Zamecnik PC, Castronovo FP, Jr, Strauss HW, Rapaport E: 99mTc-labeled nucleotides as tumor-seeking radiodiagnostic agents. Proc Natl Acad Sci USA. 1984; 81(3): 918-92.
3. Elmaleh D R, Narula J, Babich J W, Petrov A, Fischman A J, Khaw B A, Rapaport E, Zamecnik P C: Rapid noninvasive detection of experimental atherosclerotic lesions with novel 99mTc-labeled diadenosine tetraphosphates. Proc Natl Acad Sci USA. 1998; 95(2): 691-695.
4. Elmaleh D R, Fischman A J, Tawakol A, Zhu A, Shoup T M, Hoffman U, Brownell A-L, Zamecnik P C: Detection of inflamed atherosclerotic regions with diadenosine-5',5'''-P1,P4-tetraphosphate (Ap4A) and positron emission tomography. Proc Nat Acad Sci USA 2006; 103(43): 15992-15996.
5. Cheng Y, Yang J, Agarwal R, Green G M, Mease R C, Pomper M G, Meltzer S J, Abraham JM.: Strong Inhibition of Xenografted Tumor Growth by Low-Level Doses of [32P]ATP. Oncotarget. 2011 June; 2(6): 461-466.
6. Guns P J, Hendrickx J, Van Assche T, Fransen P, Bult H.: P2Y receptors and atherosclerosis in apolipoprotein E-deficient mice. *Br J Pharmacol.* 2010 Jan. 1; 159(2): 326-36.
7. Khakh B S, Burnstock G.: The double life of ATP. Sci Am. 2009; December; 301(6): 84-90, 92
8. E Rapaport, P C Zamecnik, and E F Baril: HeLa cell DNA polymerase alpha is tightly associated with tryptophanyl-tRNA synthetase and diadenosine 5',5'''-P1,P4-tetraphosphate binding activities. Proc Nat Acad Sci USA 1981; 78(2): 838-842.
9. Kukulska A, Krajewska J, Gawkowska-Suwińska M, Puch Z, Paliczka-Cieslik E, Roskosz J, Handkiewicz-Junak D, Jarzab M, Cubala E, Jarzab B.: Radioiodine thyroid remnant ablation in patients with differentiated thyroid carcinoma (DTC): prospective comparison of long-term outcomes of treatment with 30, 60 and 100 mCi. *Thyroid Res.* 2010 Nov. 1; 3(1): 9, 1-4.
10. Feng L, Sun X, Csizmadia E, Han L, Bian S, Murakami T, Wang X, Robson S C, Wu Y.: Vascular CD39/ENTPD1 directly promotes tumor cell growth by scavenging extracellular adenosine triphosphate. Neoplasia. 2011 March; 13(3): 206-216.
11. U.S. Pat. No. 4,880,918
12. U.S. Pat. No. 5,049,372
13. U.S. Pat. No. 6,299,857
14. U.S. Pat. No. 7,671,038
15. U.S. Pat. No. 7,879,814
16. U.S. Pat. No. 7,919,108

Having thus described our invention, what we claim as new and useful and desire to Secure by Letters Patent is:

1. A method for treating cardiovascular disease or atherosclerosis or vascular inflammation or stenosis by administering 32P-radioactively-labeled adenosine 5'-triphosphate; or pharmaceutically accepted salt thereof; or metal complex thereof; or chelate thereof; or liposome thereof to a human patient suffering from cardiovascular disease or artherosclerosis or vascular inflammation or stenosis, and wherein the 32P-radioactively-labeled adenosine 5'-triphosphate has a specific radioactivity of from 100-6,000 Curies/mmol and is administered to said patient in an amount per cycle of from 0.1-100 milliCuries.

2. The method of claim 1 wherein cardiovascular disease is treated in a human patient by administering 32P-radioactively-labeled adenosine 5'-triphosphate to a patient suffering from cardiovascular disease.

3. The method of claim 1, wherein atherosclerosis is treated in a human patient by administering 32P-radioactively-labeled adenosine 5'-triphosphate to a patient suffering from artheroschlerosis.

4. The method of claim 1 wherein vascular inflammation is treated in a human patient by administering 32P-radioactively-labeled adenosine 5'-triphosphate to a patient suffering from vascular inflammation.

5. The method of claim 1, wherein stenosis is treated in a human patient by administering 32P-radioactively-labeled adenosine 5'-triphosphate to a patient suffering from stenosis.

6. The method of claim 1, wherein the 32P-radioactively-labeled adenosine 5'-triphosphate is administered by intravenous infusion.

7. The method of claim 1, wherein the 32P-radioactively-labeled adenosine 5'-triphosphate is administered by injection.

8. The method of claim 1 wherein treating cardiovascular disease or atherosclerosis or vascular inflammation or stenosis in a human patient with 32P-radioactively-labeled adenosine 5'-triphosphate is performed in cycles of administration to a patient suffering from cardiovascular disease or artherosclerosis or vascular inflammation or stenosis.

9. The method of claim 1, wherein the 32P-radioactively-labeled adenosine 5'-triphosphate is administered in 1-500 milliliters of normal saline, or phosphate buffered saline or a balanced salt solution and is administered by intravenous infusion.

10. The method of claim 1 wherein said 32P-radioactively-labeledadenosine 5'-triphosphate is selected from a group consisting of 32P-radioactively-labeled [alpha-32P]adenosine 5'- triphosphate or 32P-radioactively-labeled [gamma-32P]adenosine 5'-triphosphate or pharmaceutically accepted salt thereof or metal complex thereof or chelate thereof or liposome thereof.

11. The method of claim 1 wherein said 32P-radioactively-labeledadenosine 5'-triphosphate is 32P-radioactively-labeled [alpha-32P]adenosine 5'-triphosphate or pharmaceutically accepted salt thereof or metal complex thereof or chelate thereof or liposome thereof.

12. The method of claim 1 wherein said 32P-radioactively-labeledadenosine 5'-triphosphate is 32P-radioactively-labeled [gamma-32P]adenosine 5'-triphosphate or pharmaceutically accepted salt thereof or metal complex thereof or chelate thereof or liposome thereof.

* * * * *

UNITED STATES PATENT AND TRADEMARK OFFICE
CERTIFICATE OF CORRECTION

PATENT NO.      : 8,303,934 B2
APPLICATION NO. : 13/185083
DATED           : November 6, 2012
INVENTOR(S)     : Eliezer Rapaport It is certified that error appears in the above-identified patent and that said Letters Patent is hereby corrected as shown below:

In the Claims:

Column 8, Claim 10, line 48, "labeledadenosine" should read --labeled adenosine--;

Column 8, Claim 11, line 55, "labeledadenosine" should read --labeled adenosine--;

and

Column 8, Claim 12, line 60, "labeledadenosine" should read --labeled adenosine--.

Signed and Sealed this
Eighth Day of January, 2013

David J. Kappos
*Director of the United States Patent and Trademark Office*